United States Patent
Reed et al.

(10) Patent No.: US 9,433,591 B2
(45) Date of Patent: Sep. 6, 2016

(54) NANOPARTICLES OF A METAL AND A BIGUANIDE

(71) Applicant: CERION, LLC, Rochester, NY (US)

(72) Inventors: Kenneth Joseph Reed, Rochester, NY (US); Ashley Renée Versaggi, Scottsville, NY (US); Wendi Ann Costanzo, Webster, NY (US)

(73) Assignee: CERION, LLC, Rochester, NY (US)

( * ) Notice: Subject to any disclaimer, the term of this patent is extended or adjusted under 35 U.S.C. 154(b) by 52 days.

(21) Appl. No.: 14/597,678

(22) Filed: Jan. 15, 2015

(65) Prior Publication Data
US 2015/0196510 A1 Jul. 16, 2015

Related U.S. Application Data

(60) Provisional application No. 61/964,801, filed on Jan. 15, 2014.

(51) Int. Cl.
| | |
|---|---|
| *B82Y 30/00* | (2011.01) |
| *A61K 31/155* | (2006.01) |
| *A61K 33/00* | (2006.01) |
| *A61K 9/51* | (2006.01) |
| *B82Y 40/00* | (2011.01) |
| *B82Y 5/00* | (2011.01) |

(52) U.S. Cl.
CPC ........... *A61K 31/155* (2013.01); *A61K 9/5192* (2013.01); *A61K 33/00* (2013.01); *A61K 9/5115* (2013.01); *A61K 9/5123* (2013.01); *B82Y 5/00* (2013.01); *B82Y 30/00* (2013.01); *B82Y 40/00* (2013.01)

(58) Field of Classification Search
CPC ....................................................... B82Y 30/00
USPC .................................................. 977/773, 777
See application file for complete search history.

(56) References Cited

U.S. PATENT DOCUMENTS

2007/0254994 A1  11/2007  Giannelis et al.

FOREIGN PATENT DOCUMENTS

WO    WO 2012/129279    9/2012

*Primary Examiner* — Raymond Henley, III
(74) *Attorney, Agent, or Firm* — Ratnerprestia

(57) ABSTRACT

A process for making nanoparticles of biocompatible materials is described, wherein an aqueous reaction mixture comprising a metal ion, a biguanide, an oxidant, and water; optionally further comprising an alpha-amino acid or a nucleobase; is provided along with temperature conditions to directly form within the reaction mixture, a stable dispersion of metal-containing nanoparticles. Biocompatible nanoparticles comprised of cerium and a biguanide, and optionally containing an alpha-amino acid or a nucleobase, are also described. The use of metal oxide nanoparticles comprising a biguanide as a nanoparticle core/corona in the preparation of nanoscale ionic (liquid) material compositions is disclosed.

20 Claims, No Drawings

NANOPARTICLES OF A METAL AND A BIGUANIDE

CROSS-REFERENCE TO RELATED APPLICATIONS

This application claims the benefit of U.S. Provisional Patent Application Ser. No. 61/964,801, NANOPARTICLES OF A METAL AND A BIGUANIDE, filed Jan. 15, 2014, the disclose of which is incorporated herein by reference.

FIELD OF THE INVENTION

The present invention relates in general to improvements in the fields of nanoscience. In particular, the invention relates to methods of preparing nanoparticles, to nanoparticles comprising biocompatible materials, to nanoscale ionic material compositions, and to the use of inorganic metal oxide nanoparticles as cores in the preparation of nanoscale ionic material compositions.

BACKGROUND OF THE INVENTION

Nanoparticles have shown great promise as therapeutic agents and as delivery agents for other drugs. Similarly, nanoparticles of organic-inorganic composites are attractive because they combine the low mass, low cost, ease of processing of polymer organics with the unique functionality of metal centers. However, there remains a need in the art of nanoparticle preparation to overcome poor miscibility, dispersion stability and interfacial strength problems that often limit the practical end use of many nanoparticle formulations.

The discovery of nanoscale ionic material (NIM) compositions, as described by E. P. Giannelis and A. B. Bourlinos in US Patent Application 2007/0254994, and by N. Fernandes and E. P. Giannelis in WO 2012129279, is one solution to the problem of poor nanoparticle dispersion stability in that the agglomeration of individual nanoparticles is prevented by the direct chemical tethering of a polymeric solvent (canopy) to individual nanoparticles (inorganic metal oxide core and stabilizing corona). In a particular embodiment, the NIM compositions spontaneously form nanoscale ionic liquid (NIL) material compositions that are characterized by transport and free flowing fluid properties remarkably similar to those of simple molecular liquids, but with negligible vapor pressures. There remains a need in this art for new inorganic metal oxide cores and for novel coronas to which the solvent canopy can be applied.

In addition, there remains a need for processes that directly prepare dispersions of metal oxide nanoparticles, for example, without isolation of the nanoparticles, in higher yield, in a shorter period of time and at higher suspension densities, that are biocompatible and sufficiently small in particle size (e.g. sufficiently small in size to evade detection by an immune system when administered as a drug), uniform in size frequency distribution, and stable in a wide range of biological media.

SUMMARY OF THE INVENTION

In accordance with a first aspect the invention, a process of making a dispersion of nanoparticles is provided, comprising: forming a reaction mixture comprising a metal ion, a biguanide, an oxidant, and water; optionally further comprising an alpha-amino acid or a nucleobase; heating or cooling the reaction mixture, and directly forming in the reaction mixture a dispersion of metal-containing nanoparticles.

In a second aspect of the invention, a nanoparticle comprising a metal ion and a biguanide, optionally further comprising an alpha-amino acid or a nucleobase, is provided.

In a third aspect of the invention, a metal-containing nanoparticle prepared in the presence of a biguanide, optionally further prepared in the presence of an alpha-amino acid or a nucleobase, is provided.

In a fourth aspect of the invention, a nanoscale inorganic ionic material composition comprising an organic polymer material canopy, an inorganic nanoparticle core and a stabilizing corona, wherein the inorganic nanoparticle core and stabilizing corona is comprised of or derived from a metal-containing nanoparticle prepared in the presence of a biguanide, optionally further prepared in the presence of an alpha-amino acid or a nucleobase, is provided.

In a fifth aspect of the invention, a method of making a nanoscale inorganic ionic material composition comprising adding an organic polymer material canopy to an inorganic nanoparticle core and a stabilizing corona, wherein the inorganic nanoparticle core and stabilizing corona is comprised of or derived from a metal-containing nanoparticle prepared in the presence of a biguanide, optionally further prepared in the presence of an alpha-amino acid or a nucleobase, is provided.

DETAILED DESCRIPTION OF THE INVENTION

It is to be understood that elements not specifically shown or described may take various forms well known to those skilled in the art. The invention is defined by the claims.

In this application, the term nanoparticle includes particles having a mean diameter of less than 100 nm. For the purposes of this disclosure, unless otherwise stated, the diameter of a nanoparticle refers to its average crystallographic particle diameter, which can be estimated by a peak width analysis of powder X-ray diffraction (XRD) spectra using the Scherrer equation. Alternatively, the geometric particle diameter can be estimated by analysis of transmission electron micrographs (TEM). Alternatively, the hydrodynamic diameter, which includes molecular adsorbates and the accompanying solvation shell of the particle, can be determined by dynamic light scattering techniques. In addition, for substantially monodisperse nanoparticle size distributions having geometric size in the 1-10 nm range, XRD can also reveal a very low angle scattering peak that is a direct measure of size of the scattering centers.

In this disclosure, the term "metal" in referring to elements of the Periodic Table includes all elements other than those of the following atomic numbers: 1-2, 5-10, 14-18, 33-36, 52-54, 85 and 86.

The term "transition metal" is understood to encompass the 30 chemical elements of atomic number 21 to 30, 39 to 48, 57, and 72 to 80, which are included in Periods 4, 5, 6, respectively, of the Periodic Table.

The term "rare earth metal" is understood to encompass the 14 lanthanide chemical elements of atomic number 58 to 71, and the 14 actinide chemical elements of atomic number 90 to 103.

The term "alkali metal" is understood to encompass the 6 chemical elements forming Group 1 of the Periodic Table, those of atomic number 3, 11, 19, 37, 55, and 87.

The term "alkaline earth metal" is understood to encompass the 6 chemical elements forming Group 2 of the Periodic Table, those of atomic number 4, 12, 20, 38, 56, and 88.

In this application, the term "crystalline" is understood to describe a material that displays at least one X-ray or electron diffraction peak (excluding very low angle XRD peaks not assignable to a crystal structure), wherein the peak intensity is discernibly greater than the background scattering (baseline noise). The terms "semi-crystalline" or "partially crystalline" are understood to describe a material that displays only broad X-ray or electron diffraction peaks of low peak intensity due to a lack of long-range order. The term "amorphous" is understood to describe a material that does not display any X-ray or electron diffraction peaks (excluding very low angle XRD peaks not assignable to a crystal structure).

In this application, various cerium-containing materials are nominally described as a "ceria" phase, "cerium oxide" phase or "cerium dioxide" phase. It will be understood by one skilled in the chemical arts, that the actual oxidic anions present in these materials may comprise oxide anions or hydroxide anions, or mixtures thereof, such as hydrated oxide phases (e.g. oxyhydroxide). In addition, it is known that compositions of matter may be comprised of solid solutions of multivalent cations, and are termed non-stoichiometric solids. Thus, for bulk metal oxide phases comprised of metal cations of multiple oxidation states, it is understood that the total amount of oxidic anions present will be determined by the specific amounts of the various oxidation states of the metal cations present, for example, cerous ion ($Ce^{3+}$) and ceric ion ($Ce^{4+}$), such that charge neutrality is maintained. For non-stoichiometric phases nominally described as metal dioxides, this is embodied in the chemical formula $MO_{2-\delta}$, wherein the value of δ (delta) may vary.

For a cerium oxide, $CeO_{2-\delta}$, the value of δ (delta) typically ranges from 0.0 to 0.5, the former denoting cerium (IV) oxide, $CeO_2$, the latter denoting cerium (III) oxide, $Ce_{1.5}$ (alternatively denoted $Ce_2O_3$). While not wishing to be held to any particular theory, the value of δ (delta) may be interpreted as the amount of oxygen vacancies present relative to cerium (IV) oxide ($CeO_2$). For each oxygen di-anion vacancy present, two cerous ions ($Ce^{3+}$) may be present, to preserve particle charge neutrality.

In this application, the term "cerium dioxide" is understood to describe Cerium (IV) oxide ($CeO_2$).

In this application, the term "ceria" is understood to describe a cerium oxide comprising ceric ion (i.e. $Ce^{4+}$ or cerium (IV) ion), encompassing a range of non-stoichiometric materials described by the chemical formula, $CeO_{2-\delta}$, wherein the value of δ (delta) ranges from 0.0 to less than 0.5.

In this application, the terms "nanoceria particles" and "ceria nanoparticles" have the same meaning and are used interchangeably.

In this application, the terms "dispersion", "suspension" and "colloid" have the same meaning, and are used interchangeably.

Although nominally described as "iron oxide", it is understood by one skilled in the chemical arts that there are sixteen known iron oxides and oxyhydroxides that fall into this family. In the present invention, an iron oxide may comprise oxides, wherein the iron cation is in the 2+ oxidation state or 3+ state, or mixtures thereof, such as iron (II, III) oxide or magnetite ($Fe_3O_4$), and iron (III) oxide or maghemite ($Fe_2O_3$) and /or combinations of both. Also included are hydrated oxide phases (e.g. oxyhydroxide, FeOOH). In addition, compositions of matter comprising solid solutions of multivalent cations are often termed non-stoichiometric solids. Thus, for oxide phases comprised of metal cations of multiple oxidation states along with cation vacancies, it is understood that the total amount of oxidic anions will be determined by the specific amounts of the various oxidation states of the metal cations present (e.g. $Fe^{3+}$, $Fe^{2+}$, or □, where □ indicates a cation vacancy), such that charge neutrality is maintained. For non-stoichiometric phases nominally described as metal trioxides, this is embodied in the chemical formula, $Fe^{3+}_{8A}[Fe^{3+}_{5.3}\square_{2.7} Fe^{3+}_{8}]_B O_{32}$ wherein the amount of □ may vary with particle size.

Magnetite ($Fe_3O_4$) differs from most iron oxides in that it contains both divalent and trivalent iron, and is frequently non-stoichiometric. When stoichiometric, the ratio of Fe (II)/Fe (III)=0.5. The spin arrangement is often written as $Fe^{3+}[Fe^{3+}Fe^{2+}]O_4$. The divalent iron may be partially or fully replaced by other divalent ions and is assisted by the flexibility of the oxygen framework, which can expand and contract to accommodate guest cations. Particles smaller than 6 nm are superparamagnetic at room temperature.

Maghemite has a cubic structure similar to that of magnetite except that all or most of the Fe is in the trivalent state. Cation vacancies compensate for the oxidation of Fe(II). The accepted formula for maghemite is $Fe^{3+}_{8A}[Fe^{3+}_{5.3}\square_{2.7} Fe^{3+}_{8}]_B O_{32}$, wherein A denotes tetrahedral cation sites, B denotes octahedral cation sites, and □ represents a cation vacancy. Particles less than 10 nm are superparamagnetic at room temperature.

In accordance with one aspect of the invention, a process is provided comprising: forming a reaction mixture comprising a metal ion, a biguanide, an oxidant, and water; optionally heating or cooling the mixture, and thereby forming a dispersion of nanoparticles in the reaction mixture.

In various embodiments, the reaction mixture or nanoparticles formed comprise a transition metal ion, a rare earth metal ion, an alkaline earth metal ion or an alkali metal ion.

In a particular embodiment, a process is provided comprising: forming a reaction mixture comprising cerous ion, a biguanide, an oxidant, and water; optionally heating or cooling the mixture, and thereby forming a dispersion of nanoparticles in the reaction mixture.

In a particular embodiment, a process is provided comprising: forming a reaction mixture comprising ferrous ion, a biguanide, optionally an oxidant, and water; optionally heating the mixture, and thereby forming a dispersion of nanoparticles in the reaction mixture.

In particular embodiments, the reaction mixture further comprises an alpha-amino acid or a nucleobase. In a particular embodiment, the alpha-amino acid is arginine. In particular embodiments, the nucleobase is a purine, such as, adenine, or a pyrimidine, such as, thymine.

In a particular embodiment, the reaction mixture further comprises a combination of nucleobases, such as, for example, a combination of a purine and a pyrimidine. In a particular embodiment, the reaction mixture further comprises adenine and thymine.

In a particular embodiment, the biguanide is added to the reaction mixture after the addition of the metal ion, oxidant, optional addition of an alpha-amino acid or nucleobase, and water, optionally heating or cooling of the mixture, and thereby forming a dispersion of nanoparticles in the reaction mixture. In a particular embodiment, the biguanide is chemically bonded to an alpha-amino acid or a nucleobase, such that the alpha-amino acid or nucleobase acts as a linking group to attach the biguanide to a metal-containing nanoparticle or a metal oxide nanoparticle.

In a particular embodiment, a process is provided comprising: forming a reaction mixture comprising cerous ion, ferrous ion, a biguanide, an oxidant, and water; optionally heating the mixture, and thereby forming a dispersion of nanoparticles in the reaction mixture. In various embodiments, the molar ratio of cerous ion to ferrous ion in the reaction mixture ranges from about 0.1 to about 10.0. In specific embodiments, molar ratio of cerous ion to ferrous ion in the reaction mixture is 0.11, 0.25, 0.43, 0.67, 1.0, 1.5, 2.33, 4.0 and 9.0.

In a particular embodiment, the dispersion of nanoparticles is formed directly in the reaction mixture (i.e. in situ), without precipitation or isolation of the nanoparticles.

In particular embodiments, the reaction mixture is heated or cooled to a temperature in the range of about 0° C. to about 100° C. In particular embodiments, the reaction mixture is heated or cooled to temperatures greater than 20° C., or less than or equal to 20° C. In various embodiments, the reaction mixture is heated or cooled to temperatures greater than about 30° C., about 40° C., about 50° C., about 60° C., about 70° C., about 80° C. or about 90° C.

In embodiments employing elevated reaction temperatures, the duration of time at elevated temperature may vary widely, for example, from minutes to hours. In particular embodiments, a reaction temperature in the range of about 40° C. to about 95° C. is maintained for a time ranging from about 10 minutes to about 4 hours.

In particular embodiments, the nanoparticles formed are dehydrated, dehydroxylated or deprotonated by heating of the reaction mixture.

In a particular embodiment, the crystallinity of the nanoparticles formed is enhanced by heating of the reaction mixture.

In accordance with at least one embodiment, the biguanide may comprise more than one biguanide compound, e.g., a mixture of two or more biguanide compounds.

In various embodiments, the biguanide comprises biguanide ($C_2H_7N_5$, CAS No. 56-03-01), substituted derivatives or salts (e.g. hydrochloride salt) thereof.

In particular embodiments, the biguanide is N,N-dimethylbiguanide (DMBG, CAS No. 657-24-9) or the hydrochloride salt (CAS 56258-19-6) thereof. DMBD is also known by the chemical name N,N-dimethylimidodicarbonimidic diamide, or the pharmaceutical name Metformin.

In a particular embodiment, the biguanide is 2-(N-phenethylcarbamimidoyl)guanidine ($C_{10}H_{15}N_5$, CAS No. 114-86-3), also known by the pharmaceutical name Phenformin.

In a particular embodiment, the biguanide is N-butylimidocarbonimidic diamide ($C_6H_{15}N_5$, CAS No. 692-13-7), also known by the pharmaceutical name Buformin.

In a particular embodiment, the biguanide is 1-(4-chlorophenyl)-2-(N'-propan-2-ylcarbamimidoyl)guanidide ($C_{11}H_{16}ClN_5$, CAS No. 500-92-5), also known by the pharmaceutical name Proguanil.

In a particular embodiment, the biguanide is 1-(4-chlorophenyl)-6,6-dimethyl-1,3,5-triazine-2,4-diamine ($C_{11}H_{14}ClN_5$, CAS No. 516-21-2), also known by the pharmaceutical name Cycloguanil.

In various embodiments, the oxidant comprises compounds more oxidizing than molecular oxygen (or an ambient atmosphere of air). In particular embodiments, the oxidant has an aqueous half-cell reduction potential greater than −0.13 volts relative to the standard hydrogen electrode. In specific embodiments the oxidant is an alkali metal or ammonium perchlorate, chlorate, hypochlorite or persulfate; ozone, a peroxide, such as hydrogen peroxide ($H_2O_2$) or tent-butyl hydroperoxide; or a combination thereof.

In various embodiments, the amount of oxidant employed varies widely in relation to the total amount of oxidizable metal ions present. In particular embodiments the molar amount of oxidant present is equal to or greater than the total molar amount of oxidizable metal ions. In specific embodiments, two-electron oxidants, such as hydrogen peroxide, are present in at least one-half the molar concentration of total oxidizable metal ions, such as cerous ion or ferrous ion.

In various embodiments, the oxidant is added to the reaction mixture alone or concurrently with one or more of the other reactants.

In a particular embodiment, molecular oxygen is present or passed through the reaction mixture.

In various embodiments, the nanoparticles are used to treat biological tissues or biological media, and are adjusted to physiological pH conditions ranging from about 6.5 to about 8.0, or from about 7.0 to about 7.4.

In particular embodiments, the reaction mixture is adjusted to a pH within suitable physiological conditions. In other embodiments, the final product dispersion of metal-containing nanoparticles is adjusted to a pH within suitable physiological conditions.

In various embodiments, the reaction mixture is formed in a batch reactor, a continuous reactor or a colloid mill. In particular embodiments of a continuous reactor, a continuous-stirred-tank reactor or a plug-flow reactor are used.

The particular embodiments, various mixing devices known in the art are employed to stir, mix, shear or agitate the contents of the reaction mixture. In various embodiments, mixers comprising stir bars, marine blade propellers, pitch blade turbines or flat blade turbines, or static mixers are used. In particular embodiments, a colloid mill or a Silverson® High Shear Mixer is employed. In a particular embodiment, a high shear mixer that forces the reaction mixture to pass through a screen, wherein holes vary in size from fractions of a millimeter to several millimeters, is employed. In particular embodiments, one or more of the reactants is introduced below the surface of the aqueous reaction mixture. In a particular embodiment, a reactant is introduced below the surface of the aqueous reaction mixture in close proximity to a mixing device.

In various embodiments, the nanoparticles formed are amorphous, semi-crystalline or crystalline. In a particular embodiment, the dispersion of nanoparticles formed may be comprised by individual crystallites, alternatively described as single particle crystallites. In particular embodiments, the nanoparticles formed are characterized by a cerium oxide crystal structure. In a particular embodiment the nanoparticles formed are characterized by a cubic fluorite crystal structure.

In various embodiments, the nanoparticles formed have a hydrodynamic diameter less than 100 nm, less than 80 nm, less than 60 nm, less than 40 nm, less than 20 nm, less than 10 nm, less than 5.0 nm or less than about 2.0 nm.

In a particular embodiment of the invention, a nanoparticle comprising a metal and a biguanide, optionally further comprising an alpha-amino acid or a nucleobase, is provided.

In a particular embodiment of the invention, a nanoparticle comprising a metal oxide and a biguanide, optionally further comprising an alpha-amino acid or a nucleobase, is provided.

In a particular embodiment of the invention, a nanoparticle comprising cerium and a biguanide, optionally further comprising an alpha-amino acid or a nucleobase, is provided.

In a particular embodiment, a nanoparticle comprising ceric ion and a biguanide, optionally further comprising an alpha-amino acid or a nucleobase, is provided.

In a particular embodiment, a nanoparticle comprising ceria and a biguanide, optionally further comprising an alpha-amino acid or a nucleobase, is provided.

In a particular embodiment, a nanoparticle comprising a biguanide and a cerium oxide, cerium hydroxide or cerium oxyhydroxide, optionally further comprising an alpha-amino acid or a nucleobase, is provided.

In a particular embodiment of the invention, a nanoparticle comprising iron and a biguanide, optionally further comprising an alpha-amino acid or a nucleobase, is provided.

In a particular embodiment, a nanoparticle comprising ferric ion and a biguanide, optionally further comprising an alpha-amino acid or a nucleobase, is provided.

In a particular embodiment, a nanoparticle comprising ferrous ion and a biguanide, optionally further comprising an alpha-amino acid or a nucleobase, is provided.

In a particular embodiment, a nanoparticle comprising an iron oxide and a biguanide, optionally further comprising an alpha-amino acid or a nucleobase, is provided.

In a particular embodiment, a nanoparticle comprising a biguanide and an iron oxide, iron hydroxide or iron oxyhydroxide, optionally further comprising an alpha-amino acid or a nucleobase, is provided.

In various embodiments, the zeta potential of the nanoparticle dispersion formed is altered by adjusting the pH, the biguanide content, or a combination thereof.

In a particular embodiment, the nanoparticle dispersion formed is washed to remove excess ions or by-product salts. In various embodiments, the nanoparticle dispersion is washed such that the ionic conductivity is reduced to less than about 40 millisiemens per centimeter (mS/cm), less than about 20 mS/cm, less than about 10 mS/cm, less than about 5 mS/cm or less than about 3 mS/cm. In particular embodiments, the nanoparticle dispersion formed is washed without isolation of the nanoparticles, such as, for example, by dialysis or diafiltration, thereby maintaining the nanoparticle dispersion stability.

In particular embodiments, the nanoparticle dispersions formed are concentrated to remove excess solvent or excess water. In particular embodiments, the nanoparticle dispersion is concentrated by diafiltration or centrifugation.

In various embodiments, the concentration of nanoparticles in the dispersion is greater than about 0.05 molal, greater than about 0.5 molal or greater than about 2.0 molal (approximately 35% solids in a given dispersion).

In particular embodiments, the size distribution of the nanoparticles is substantially monomodal. In various embodiments, the nanoparticle size distribution has a coefficient of variation (COV) less than about 30%, less than about 25%, less than about 20%, less than about 15%, less than about 10% or less than about 5%, where the COV is defined as the standard deviation divided by the mean.

In particular embodiments, a pharmaceutical composition comprises nanoparticles comprising a metal and a biguanide, optionally further comprising an alpha-amino acid or a nucleobase.

In particular embodiments, a pharmaceutical composition comprises nanoparticles comprising metal oxide nanoparticles prepared in the presence of a biguanide, optionally further prepared in the presence of an alpha-amino acid or a nucleobase.

In particular embodiments, a pharmaceutical composition comprises nanoparticles comprising ceria and a biguanide, optionally further comprising an alpha-amino acid or a nucleobase.

In particular embodiments, a pharmaceutical composition comprises nanoparticles comprising ceria nanoparticles prepared in the presence of a biguanide, optionally further prepared in the presence of an alpha-amino acid or a nucleobase.

In particular embodiments, a pharmaceutical composition comprises nanoparticles comprising ceria and a biguanide, optionally further comprising an alpha-amino acid or a nucleobase, or, ceria nanoparticles prepared in the presence of a biguanide, optionally further prepared in the presence of an alpha-amino acid or a nucleobase, wherein the composition is used as a cytoprotective reagent.

In particular embodiments, a pharmaceutical composition comprises nanoparticles comprising an iron oxide and a biguanide, optionally further comprising an alpha-amino acid or a nucleobase, or, iron oxide nanoparticles prepared in the presence of a biguanide, optionally further prepared in the presence of an alpha-amino acid or a nucleobase.

In particular embodiments, a pharmaceutical composition comprises nanoparticles comprising an iron oxide and a biguanide, optionally further comprising an alpha-amino acid or a nucleobase, or, iron oxide nanoparticles prepared in the presence of a biguanide, optionally further prepared in the presence of an alpha-amino acid or a nucleobase, wherein the composition is used as a cytotoxic reagent.

In various embodiments, a pharmaceutical composition comprises nanoparticles comprising ceria or an iron oxide and a biguanide, optionally further comprising an alpha-amino acid or a nucleobase, or, nanoparticles comprising ceria or an iron oxide prepared in the presence of a biguanide, optionally further prepared in the presence of an alpha-amino acid or a nucleobase, is administered to a human or a non-human subject, such as another mammal, including, but not limited to, a canine, a feline, a bovine, an equine, an ovine, a porcine or a rodent. Alternatively, the subject of administration can be an animal such as a bird, insect, reptile, amphibian, or any companion or agricultural animal. Alternatively, the subject of administration can be a bacterium, yeast, mold, fungus or another single celled organism. The subject of administration can also be a plant.

Pharmaceutical compositions according to the present disclosure, may further comprise at least one pharmaceutically acceptable excipient.

In another particular embodiment, a process of preventing (i.e. prophylactically treating) an oxidative stress related event, disease or cellular pathology, comprises administering prior to the onset of such an event, disease or cellular pathology, an effective amount of a ceria or iron oxide nanoparticle prepared in the presence of a biguanide, optionally further prepared in the presence of an alpha-amino acid or a nucleobase, or, a nanoparticle comprising ceria and a biguanide, optionally further comprising an alpha-amino acid or a nucleobase. In a particular embodiment, the cellular pathology prevented (i.e. prophylactically treated) is diabetes.

In another particular embodiment, a process of treating an oxidative stress related event, disease or cellular pathology, comprises administering after the onset of an event, disease or cellular pathology, an effective amount of a ceria nanoparticle or iron oxide nanoparticle prepared in the presence of a biguanide, optionally further prepared in the presence of an alpha-amino acid or a nucleobase, or, a nanoparticle comprising ceria and a biguanide, optionally further comprising an alpha-amino acid or a nucleobase. In a particular embodiment, the cellular pathology prevented (i.e. prophylactically treated) is diabetes.

In another end-use application, the various metal-containing and biguanide-containing nanoparticles of the invention, optionally further comprising an alpha-amino acid or a nucleobase, as described supra, are specifically contemplated for use as a nanoparticle core or as an inorganic metal oxide core in the preparation of a nanoscale ionic material (NIM) composition. The preparation of NIM compositions is described in general, for example, by E. P. Giannelis and A. B. Bourlinos in US 2007/0254994, which is incorporated herein by reference in its entirely, and by N. Fernandes and E. P. Giannelis in WO 2012129279, which is incorporated herein by reference in its entirely. A nanoscale ionic material (NIM) composition comprises a nanoparticle (e.g. inorganic metal oxide core and a stabilizing corona) an organic polymer material canopy. In a particular embodiment, NIM compositions spontaneously form nanoscale ionic liquid (NIL) material compositions that are characterized by transport and free flow fluid properties remarkably similar to those of simple molecular liquids, but with negligible vapor pressures. In other embodiments, NIM compositions spontaneously form nanoscale ionic solid (NIS) material compositions and nanoscale ionic gel (NIG) material compositions, the latter containing an intermediate amount of inorganic material content and organic material content, and characterized by physical and chemical properties intermediate to those of NIS material compositions and NIL material compositions.

The invention is further illustrated by the following examples, which are not intended to limit the invention in any manner.

EXPERIMENTAL SECTION

Nanoparticle Scattering and Size Assessments

A simple qualitative characterization of the particle dispersions was performed by assessing the degree of Tyndell scattering exhibited by the dispersions when illuminated by a red laser pen light, relative to the amount of scattering from a sample of the neat solvent.

Quantitative assessments of the particle size of the nanoparticle dispersions can be made by a number of techniques.

Particle size estimation by peak-width analysis of X-ray diffraction (XRD) spectra was done using the Scherrer method. Sample preparation for the XRD measurements was done as follows: liquid samples were mixed lightly, placed in a Telfon boat, allowed to dry under a heat lamp for several hours (until nearly dry), the resulting concentrated liquid was then placed onto a zero background quartz disk, allowed to dry under the heat lamp, and then dried in an oven at either room temperature or at about 80° C. for four hours under a dry nitrogen atmosphere. The coated disk was then analyzed by XRD using a nitrogen gas dry cell attachment. The XRD spectra were recorded on a Rigaku D2000 diffractometer equipped with copper rotating anode, diffraction beam graphite monochrometer tuned to copper K-alpha radiation, and a scintillation detector.

Alternatively, dynamic light scattering (DLS) measurements were obtained using a Brookhaven 90Plus Particle Size Analyzer (Brookhaven Instruments Corp., Holtzville, N.Y., U.S.A.) equipped with a quartz cuvette. Samples were typically filtered through a 0.2 micron syringe filter prior to measurement to remove bacterial contaminants. Reported DLS sizes are the lognormal number weighted parameter. These hydrodynamic particle sizes are typically larger than sizes yielded by other techniques because the DLS technique includes contributions from adsorbed ions or molecules that constitute the solvation sphere of the particle.

Alternatively, the size of the nanoparticles could be determined by direct analysis of transmission electron microscopy (TEM) images of the particles.

EXAMPLE 1

Preparation of Nanoparticles with Cerium and Dimethylbiguanide (Inventive)

AV.17.6

To a 0.6 L beaker, 500 mL of high purity (HP) water was introduced, and then 1.96 grams N,N-dimethylbiguanide hydrochloride (97%, CAS 56258-19-6) was added with stirring and gradual heating to 40° C. until dissolved. A 10.0 g quantity of $Ce(NO_3)_3.6H_2O$ dissolved in 40 mL HP water was then added to the reaction mixture under high shear mixing conditions, resulting in a mild peach/tan color and a solution pH of 5.2. The molar ratio of DMBG to cerium was 0.5. Then, a 2.4 g quantity of 50% $H_2O_2$ was diluted into 10 mL of HP water and added to the reaction mixture, which immediately turned a dark orange brown color with a pH of 3.3. After a few minutes of stirring, the reaction mixture turned a translucent tangerine orange color. The pH was then adjusted to 2.4 by nitric acid addition. The reaction mixture was held at 40° C. for 1 hour, and then cooled with stirring over night, thereby forming a product dispersion at an ionic conductivity of 14.1 mS and a final pH of 3.0.

The final reaction product was a clear light orange colored liquid that displayed a high degree of Tyndall scattering when illuminated with a low intensity LASER beam, a test for well-dispersed colloidal particles. Particle size analysis by DLS revealed a hydrodynamic particle size of 13.7 nm with a polydispersity of 0.256, indicating that a stable dispersion of nanoparticles had formed.

EXAMPLE 2

Preparation of Nanoparticles with Iron and Dimethylbiguanide (Inventive)

CNRx.01.115.1 and CNRx.01.115.2

To a 0.8 L beaker, 450 mL of high purity (HP) water was introduced, and then 2.107 grams N,N-dimethylbiguanide hydrochloride (97%, CAS 56258-19-6) was added with stirring and gradual heating to 40° C. until dissolved. A 10.0 g quantity of $Fe(NO_3)_3.9H_2O$ dissolved in 30 mL HP water was then added to the reaction mixture under high shear mixing conditions, resulting in a red color and a solution pH less than 1.0. The molar ratio of DMBG to iron was 0.5. Then, a 2.4 g quantity of 50% $H_2O_2$ was diluted into 50 mL of HP water and added to the reaction mixture, which immediately turned a darker red color with a pH less than 1.0. The reaction mixture was held at 40° C. for 1 hour, and then one half of the reaction mixture was allowed to cooled with stirring, thereby forming a product dispersion (designated Example 2a) at an ionic conductivity of 17.7 mS and a final pH of 1.0.

The second half of the reaction mixture was heated for an additional 2 hours at 80° C., and then cooled with stirring, thereby forming a product dispersion (designated Example 2b) at an ionic conductivity of 34.4 mS and a final pH less than 1.0.

The final reaction products (Examples 2a and 2b) were clear dark red colored liquids that displayed a high degree of Tyndall scattering when illuminated with a low intensity LASER beam, a test for well-dispersed colloidal particles. Particle size analysis by DLS revealed a hydrodynamic particle size of 2.6 nm with a polydispersity of 0.167 for Example 2a, and hydrodynamic particle size of 8.9 nm with a polydispersity of 0.281 for Example 2b, indicating that stable dispersions of nanoparticles had formed.

EXAMPLE 3

Preparation of Nanoparticles with Cerium, Arginine and Dimethylbiguanide (Inventive)

AV.17.4a

To a 0.6 L beaker, 500 mL of high purity (HP) water was introduced, and then 2.35 grams N,N-dimethylbiguanide hydrochloride (97%, CAS 56258-19-6) was added with stirring and gradual heating to 40° C. until dissolved. To the solution, 2.48 grams of 97% Arginine was added and dissolved. A 10.0 g quantity of $Ce(NO_3)_3.6H_2O$ dissolved in 40 mL HP water was then added to the reaction mixture, resulting in a mild peach/tan color and a solution pH of 7.9. The molar ratios of DMBG to cerium and of Arginine to cerium were 0.6. Then, a 1.2 gram quantity of 50% $H_2O_2$ was diluted into 10 mL of HP water and added to the reaction mixture, which immediately turned a dark orange brown color with a pH of 4.1. After a few minutes of stirring, the reaction mixture turned a translucent tangerine orange color. The solution pH was then adjusted to 2.55 by nitric acid addition, and the resulting color changed to translucent orange. The reaction mixture was held at 40° C. with stirring for 1 hour, and then cooled with stirring over night. The resulting product dispersion was washed to remove excess salts and unreacted starting materials via diafiltration, until a final ionic conductivity of 8.85 mS and a final pH of 3.6.

The final reaction product was a clear light orange colored liquid that displayed a high degree of Tyndall scattering when illuminated with a low intensity LASER beam, a test for well-dispersed colloidal particles. Particle size analysis by DLS revealed a hydrodynamic particle size of 8.1 nm with a polydispersity of 0.295, indicating that a stable dispersion of nanoparticles had formed.

Thus, the above example demonstrated that a stable dispersion of cerium-containing nanoparticles was formed in the presence of equimolar amounts of a biguanide and an alpha-amino acid (arginine).

EXAMPLE 4

Preparation of Nanoparticles with Cerium, Adenine, Thymine and Dimethylbiguanide (Inventive)

AV.18

To a 0.4 L beaker, 250 mL of high purity (HP) water was introduced, and then 0.207 grams of 99% Adenine, 0.194 grams of 99% Thymine, and 1.96 grams N,N-dimethylbiguanide hydrochloride (97%, CAS 56258-19-6) were added in succession with stirring and gradual heating to 40° C. until dissolved. A 5.0 g quantity of $Ce(NO_3)_3.6H_2O$ dissolved in 20 mL HP water was then added to the reaction mixture, resulting in a mild peach/tan color and a solution pH of 5.2. The molar ratio of each of adenine, thymine and DMBG to cerium was 0.33. Then, a 0.3 g quantity of 50% $H_2O_2$ was diluted into 10 mL of HP water and added to the reaction mixture, which immediately turned a clear dark orange red color. The reaction mixture was held at 40° C. for 1 hour, and then cooled with stirring over night, thereby forming a product dispersion with an ionic conductivity of 10.7 mS and a final pH of 3.9.

The final reaction product was a translucent tangerine colored liquid that displayed a high degree of Tyndall scattering when illuminated with a low intensity LASER beam, a test for well-dispersed colloidal particles. Particle size analysis by DLS revealed a hydrodynamic particle size of 16.3 nm with a polydispersity of 0.1425, indicating that a stable dispersion of nanoparticles had formed.

A portion of the final product dispersion was washed via diafiltration with an equal volume of HP water, thereby reducing the ionic conductivity to 3.96 mS at a pH of 4.3. Particle size analysis by DLS revealed a hydrodynamic particle size of 17.7 nm with a polydispersity of 0.304, indicating that the washing step did not substantially alter the measured nanoparticle size.

Thus, the above example demonstrated that a stable dispersion of cerium-containing nanoparticles was formed in the presence of equimolar amounts of a biguanide, a purine nucleobase (adenine) and a pyrimidine nucleobase (thymine).

While the invention has been described by reference to various specific embodiments, it should be understood that numerous changes may be made within the spirit and scope of the inventive concepts described. Accordingly, it is intended that the invention not be limited to the described embodiments, but will have full scope defined by the claims.

What is claimed:

1. A method of making a dispersion of nanoparticles, comprising:
   a. forming a reaction mixture comprising a metal ion, a biguanide, an oxidant, and water; and
   b. directly forming in the reaction mixture a dispersion of nanoparticles.

2. The method of claim 1, wherein said dispersion of nanoparticles is formed without precipitation or isolation of the nanoparticles.

3. The method of claim 1, further comprising heating or cooling said reaction mixture to a temperature in the range of about 0° C. to about 100° C.

4. The method of claim 1, wherein said metal ion comprises a transition metal ion, a rare earth metal ion, and alkali metal ion or an alkaline earth metal ion.

5. The method of claim 4, wherein said transition metal ion comprises a cerium ion or an iron ion.

6. The method of claim 1, wherein said biguanide comprises N,N-dimethylbiguanide or a hydrochloride salt thereof.

7. The method of claim 1, wherein said oxidant comprises a peroxide.

8. The method of claim 7, wherein said peroxide is hydrogen peroxide.

9. The method of claim 1, wherein said reaction mixture further comprises an alpha-amino acid.

10. The method of claim 9, wherein said alpha-amino acid is arginine.

11. The method of claim 1, wherein said reaction mixture further comprises a nucleobase.

12. The method of claim 1, wherein said nucleobase is adenine, thymine, or a combination thereof.

13. A nanoparticle, comprising: a metal and a biguanide.

14. The nanoparticle of claim 13, wherein said metal comprises cerium or iron.

15. The nanoparticle of claim 13, wherein said metal is a metal oxide.

16. The nanoparticle of claim 15, wherein said metal oxide is a cerium oxide or an iron oxide.

17. The nanoparticle of claim 13, wherein said biguanide comprises N,N-dimethylbiguanide.

18. The nanoparticle of claim 13, further comprising an alpha-amino acid or a nucleobase.

19. A pharmaceutical composition comprising nanoparticles comprising a metal and a biguanide.

20. The pharmaceutical composition of claim 19, wherein said nanoparticles further comprise an alpha-amino acid or a nucleobase.

* * * * *